US008048644B1

(12) United States Patent
Steck et al.

(10) Patent No.: US 8,048,644 B1
(45) Date of Patent: Nov. 1, 2011

(54) BIOLOGICAL INDICATOR FOR MONITORING THE TRANSPORT OF MICRO-ORGANISMS IN THE ENVIRONMENT

(75) Inventors: Todd R. Steck, Charlotte, NC (US); Helene A. Hilger, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 11/337,736

(22) Filed: Jan. 23, 2006

Related U.S. Application Data

(62) Division of application No. 10/135,238, filed on Apr. 30, 2002, now abandoned.

(60) Provisional application No. 60/309,049, filed on Aug. 1, 2001.

(51) Int. Cl.
| | |
|---|---|
| C12Q 1/00 | (2006.01) |
| C12Q 1/70 | (2006.01) |
| C12Q 1/68 | (2006.01) |
| C12Q 1/64 | (2006.01) |
| C12Q 1/24 | (2006.01) |
| C12Q 1/04 | (2006.01) |
| G01N 33/53 | (2006.01) |
| G01N 33/567 | (2006.01) |
| G01N 33/554 | (2006.01) |
| G01N 33/569 | (2006.01) |
| G01N 33/542 | (2006.01) |
| G01N 1/30 | (2006.01) |
| G01N 33/48 | (2006.01) |

(52) U.S. Cl. ........ 435/34; 435/4; 435/5; 435/6; 435/7.2; 435/7.32; 435/7.72; 435/9; 435/30; 435/40.5

(58) Field of Classification Search .................. None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,491,084 | A | 2/1996 | Chalfie et al. |
| 5,693,469 | A | 12/1997 | Hogan |
| 5,972,638 | A | 10/1999 | Burlage et al. |
| 6,146,826 | A | 11/2000 | Chalfie |
| 6,225,046 | B1 | 5/2001 | Vesey et al. |
| 6,436,682 | B1 * | 8/2002 | Bryan et al. .................. 435/189 |

OTHER PUBLICATIONS

Burlage et al (Gene, 1996; 173:53-58).*
Greenspan et al. (Nature Biotechnology 17: 936-937, 1999).*
Devaraj (Mechanisms of extinction-viruses; Journal of theoretics; 2000: 1-8).*
Hunt (Virology-Chapter Three; DNA Virus Replication Strategies pp. 1-8).*
Palevsky (Swine Flu, Vaccines and fear, 2009; pp. 1-5).*
Bernhard, A. E., and Field, K.G., *Applied Environmental Microbiol.* vol. 66:1587-1594 (2000).
Hagedorn, C. et al., *Applied Environmental Microbiol.* vol. 65:5522-5531 (1999).
Office Communication corresponding to U.S. Appl. No. 10/135,238 dated Dec. 2, 2003.
Office Communication corresponding to U.S. Appl. No. 10/135,238 dated Apr. 20, 2004.
Office Communication corresponding to U.S. Appl. No. 10/135,238 dated Mar. 28, 2005.
Office Communication corresponding to U.S. Appl. No. 10/135,238 dated Sep. 22, 2005.
Parveen, S., et al., *Applied Environmental Microbiol.* vol. 63:2607-2612 (1997).
Parveen, S., et al., *Applied Environmental Microbiol.* vol. 65:3142-3147 (1999).
Sinton, L.W., Finlay, R.K., and Hannah, D. J., *New Zealand J. Marine and Freshwater Res.* vol. 32:323-348 (1998).
Wiggins, B.A., *Applied Environmental Microbol.* vol. 62:3997-4002 (1996).
Wiggins, B.A., et al., *Applied Environmental Microbiol.* vol. 65:3483-3486 (1999).
Blanch et al., "Integrated Analysis of Established and Novel Microbial and Chemical Methods for Microbial Source Tracking," Applied and Environmental Microbiology, vol. 72, No. 9 pp. 5915-5926 (Sep. 2006).
Cebolla et al., "Expression vectors for the use of eukaryotic luciferases as bacterial markers with different colors of luminescence," Applied and Environmental Microbiology, vol. 61, No. 2, pp. 660-668 (Feb. 1995).
Crameri et al., "Improved Green Fluorescent Protein by Molecular Evolution Using DNA Shuffling," Nature Biotechnology, vol. 14, No. 3, pp. 315-319 (Mar. 1996).
definition "ultraviolet", On-Line Medical Dictionary, cancerweb.ncl.ac.uk/omd.
Unge et al., "Simultaneous Monitoring of Cell Number and Metabolic Activity of Specific Bacterial Populations with a Dual *gfp-luxAB* Marker System," Applied and Environmental Microbiology, vol. 65, pp. 813-821 (Feb. 1999).
DuPont et al., "Pathogenesis of *Escherichia coli* diarrhea," N. Engl. J. Med., vol. 285, pp. 1-9 (1971).
Levine et al., "*Escherichia coli* strains that cause diarrhea but do not produce heat-labile or heat-stable enterotoxins and are non-invasive," Lancet, vol. 1, pp. 1119-1122 (1978).

(Continued)

*Primary Examiner* — Vanessa L Ford
*Assistant Examiner* — Lakia Tongue
(74) *Attorney, Agent, or Firm* — Jenkins, Wilson, Taylor & Hunt, P.A.

(57) ABSTRACT

A method of using a biological indicator to detect and identify sources of fecal contamination such as leaking sewer lines, septic tanks, and holding lagoons, using a microorganism having a biological indicator including an exogenous DNA indicator sequence incorporated into the genome of the microorganism. The exogenous DNA indicator sequence functions as a detectable signal that may be detected by visual detection methods or direct detection methods of the indicator sequence itself.

10 Claims, 5 Drawing Sheets

OTHER PUBLICATIONS

McKenzie and Craig, "Fast, easy and efficient: site-specific insertion of transgenes into Enterobacterial chromosomes using Tn7 without need for selection of the insertion event," BMC Microbiology, vol. 6, ARTN 39 (2006).

Peters and Craig, "Tn7: smarter than we thought," Nat. Rev. Mol. Cell Biol., vol. 2, pp. 806-814 (2001).

Rasko et al., "The pangenome structure of *Escherichia coli* : comparative genomic analysis of *E. coli* commensal and pathogenic isolates," J. Bacteriol., vol. 190, pp. 6881-6893 (2008).

Protocol for Developing Pathogen TMDLs, First Edition, published by the Environmental Protection Agency (EPA) in Jan. 2001.

* cited by examiner

BIOLOGICAL INDICATOR FOR MONITORING THE TRANSPORT OF MICRO-ORGANISMS IN THE ENVIRONMENT

STATEMENT OF RELATED APPLICATIONS

The present application is a divisional application of U.S. patent application Ser. No. 10/135,238, filed Apr. 30, 2002 now abandoned, which claims priority under 35 USC 119 from U.S. Provisional Application Ser. No. 60/309,049 filed Aug. 1, 2001, entitled "Method Development to Determine Fecal Contaminant Source Information for TMDL Assessments," the disclosure of which is incorporated herein by reference.

BACKGROUND OF THE INVENTION

1. Field of the Invention

The present invention relates to the field of water quality control, bioremediation, biomonitoring and biocide treatment.

2. Description of Related Art

A small subset of the micro-organisms present in ecosystems is harmful to humans. These harmful micro-organisms are known as pathogens. Once in a stream, lake, or estuary, these harmful micro-organisms can infect humans through contaminated fish and shellfish, skin contact or ingestion of water. Aerosols are another mode of human contact with water-borne pathogens. Defective and improperly designed or installed septic tanks, sewage sludge land applications, and undetected sewage system leakage are major sources for pathogens in groundwater.

Pathogenic organisms are typically monitored by following non-pathogenic bacteria that are usually associated with the pathogenic organisms. These associated bacteria are called indicator organisms. Certain indicator organisms, referred to as fecal indicators, indicate the possible presence of human pathogenic organisms. These indicator organisms may also be used to assess the degree of pathogen removal by treatment processes or to detect contamination of distribution systems.

A commonly used indicator organism is coliform bacteria. Coliform bacteria include total coliforms and fecal coliforms. The term "total coliforms" includes several genera of gram-negative, facultative anaerobic, non-spore-forming, rod-shaped bacteria, some of which occur naturally in the intestinal tract of animals and humans, as well as others that occur naturally in soil and in fresh or marine waters and could be pathogenic to a variety of specific hosts. Fecal coliforms, including *Escherichia coli* ("*E. coli*"), are found in the intestines and feces of warm-blooded animals. Thus, the presence of *E. coli* in a water sample indicates fecal contamination and the possible presence of pathogens.

Efforts to reduce the amount of fecal coliforms in surface and ground waters are hindered by the uncertainty about the sources of fecal coliforms found in such waters and by an inability to link excess fecal contamination with specific sources such as sewer line leaks or wastewater treatment plant (WWTP) effluent.

Most fecal indicators are indirect and only warn of the possibility of the presence of fecal pathogens, which are not necessarily from humans, and potentially from multiple sources. This is because there are multiple bacterial species and multiple strains of a given bacterial species in the environment that can mask attempts to track a specific population of bacteria. Further, determining what happens to the micro-organisms once they reach a body of water is often as challenging as identifying and tracking their sources. As living organisms, micro-organisms require certain conditions to survive, grow, and reproduce. Many factors influence the die-off rate of viruses, bacteria, and protozoans in the environment. These factors include, but are not limited to, sunlight, temperature, moisture conditions, salinity, soil conditions, water body conditions, settling, association with particles, and encystation. Thus, there is a need for a method to unequivocally determine sources of fecal contamination and to easily track the movement of fecal contaminants in the environment. More broadly, there is a need for a method to easily track the movement and viability of micro-organisms in the environment.

One approach to identifying and tracking micro-organisms and sources of fecal contamination uses dyes or other non-living indicators. However, dyes do not necessarily behave like micro-organisms in the environment. For example, dyes do not grow and cannot reflect whether environmental conditions would have killed a living organism. In addition, dyes do not necessarily adsorb in a manner identical to micro-organisms.

A number of methodologies designed to identify the source of fecal pollution have been collectively referred to as Bacterial Source Tracking (BST) methods. BST methods provide information as to what animal the bacteria came from and not the physical source. Based on the information that BST methods provide, water quality restoration efforts can be targeted to the appropriate physical source (i.e. sewage system vs. agricultural runoff).

The BST methods can be separated into two groups based on whether the methods analyze differences in bacterial phenotype, such as outer membrane protein profiles or multiple antibiotic resistance patterns, or differences in bacterial genotype, such as restriction fragment length polymorphism, randomly amplified polymorphic DNA, or ribotyping.

All BST methods have one or more limitations to their utility in identifying specific, sources of fecal contamination. First, with all BST methods, classification of a bacterial sample as being from a human or a nonhuman source is typically reported as a probability statement, although it is unclear what minimum probability is predictive of the actual source. (Wiggins, 1996; Parveen et al., 1997; Sinton et al., 1998; Hagedom et al., 1999; Parveen et al., 1999; Wiggins et al., 1999; Bernhard and Field, 2000). Second, all BST methods are predicated on the assumption that there are differences among bacterial strains originating from human versus nonhuman sources. For example, to unambiguously identify the animal source of an unknown *E. coli* isolate, there must be a DNA sequence unique to that animal's *E. coli* isolate and the DNA sequence must be found in all *E. coli* isolates from that animal's species. However, genetic principles indicate that there is not a barrier to exchange of DNA between *E. coli* strains, regardless of animal source. As a result, definitive uniform DNA sequence differences between strains of *E. coli* should not exist when based solely on the strain's animal source. Second, many bacterial tracking or identification methods rely on being able to culture bacteria from a sample prior to performing the assay. Because most bacteria from environmental samples are in a not readily culturable form (e.g., the viable but nonculturable (VBNC) state), these culture-based assays will not detect these bacteria. Third, many BST methods examine populations of bacteria and do not follow specific bacteria; this can affect the interpretation of data obtained from an assay. For example, it is difficult to determine if bacteria present in an environmental sample originated from a putative contamination point source, or from a source located between the putative point source and the collection point (i.e. it cannot be determined what percentage of bacteria in a sample originated from the potential point source). BST methods are also typically very costly and time intensive to conduct. Because of the limitations of current methods in identifying and monitoring sources of fecal contamination with respect to specificity, accuracy, cost, and time, a need exists for a method to directly identify the physical source of contamination in a water system. More broadly, the need exists for a method to easily track the movement of and viability of micro-organisms in the environment.

SUMMARY OF THE INVENTION

The present invention relates to the creation of a genetically engineered strain of a natural isolate of a non-pathogenic micro-organism, referred to as a biological indicator, that can be released into the environment. The biological indicator of the present invention reports its location by producing a detectable signal. The detectable signal comprises an exogenous DNA indicator sequence unique to the species of the biological indicator. The detectable signal may further comprise a signal produced by an indicator protein produced by the biological indicator. The detectable signal can also be measured.

The present invention also relates to a method of monitoring for the presence of the biological indicator in environmental samples.

Methods of the present invention use the biological indicator to monitor the presence and movement of the biological indicator in and through the environment. Certain methods of the present invention use this biological indicator to detect and identify fecal contamination sources such as sewer line leaks. For example, the biological indicator of the present invention can be added to a sewer line suspected of leaking. With proper controls in place, detection of the biological indicator in soil, groundwater or streamflow adjacent to the spiked sewer line would indicate the likely presence of a sewer line leak. Such methods can provide data for state and local Total Maximum Daily Load (TMDL) plans.

Embodiments of the present invention are advantageous for identification of sources of fecal contamination from a potential polluting source or facility into adjacent surface or ground waters or the elimination of such sources from suspicion; determining the physiological state of micro-organisms in various matrices (i.e. dead, culturable, or viable but non-culturable), such as polluted water, plant surfaces, groundwater, soil, and aerosols under a variety of environmental conditions; determining the ability of coliform indicators to migrate through soils to groundwater or surface water; determining the effectiveness in the environment of biocide or anti-microbial agents aimed at killing bacteria; determining the distribution of bacteria present in materials applied to the environment via aerosol; tagging potential environmental pollution sites to identify the sources of contamination events; or any other application that involves monitoring the source, number, and physiological status of micro-organisms in the environment.

DETAILED DESCRIPTION

Figure 1:
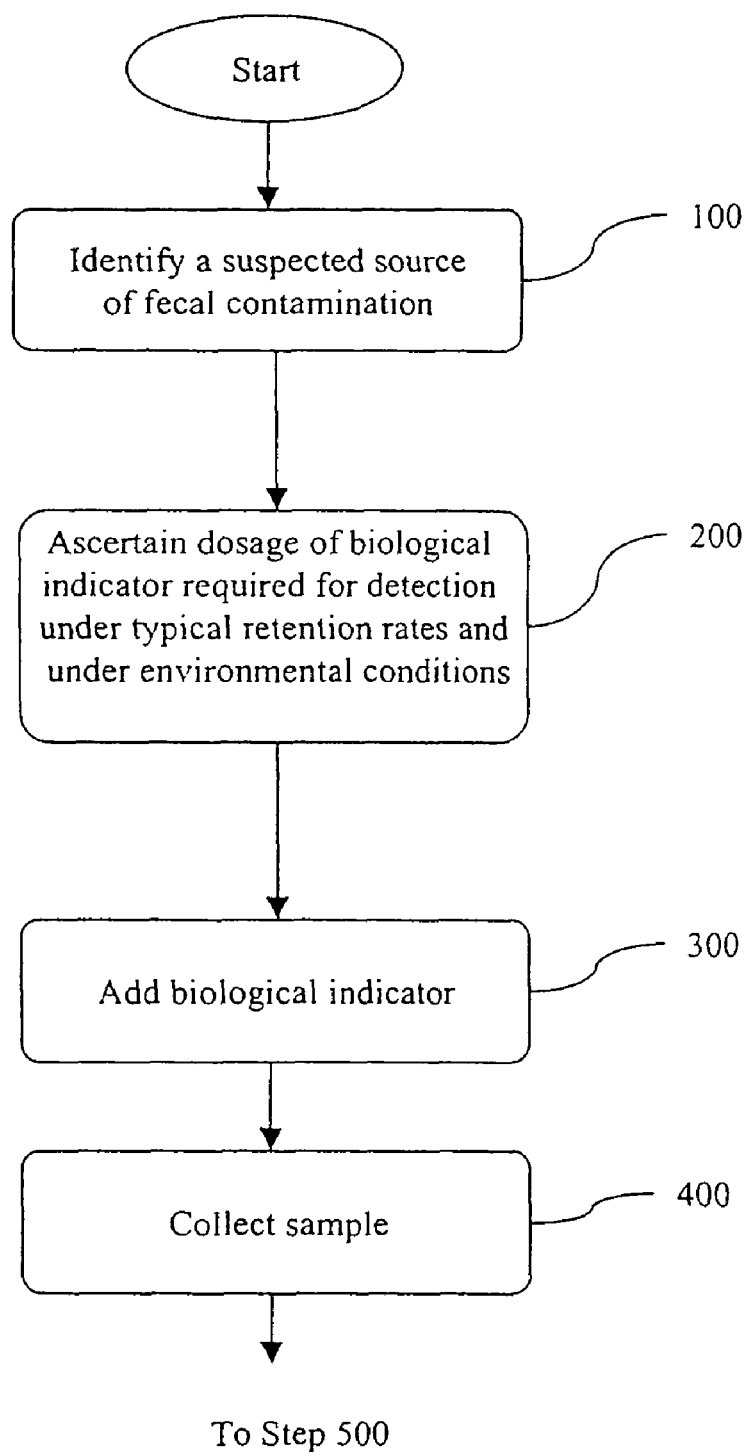
FIGS. 1 and 2 are a flow diagram of a method of the present invention.

The biological indicator of the present invention reports its location by producing a detectable signal that can be measured. The detectable signal comprises an exogenous DNA indicator sequence that is unique to the species of the biological indicator. The detectable signal may further comprise a signal produced by an indicator protein produced by the biological indicator.

Methods of the present invention use this biological indicator to monitor the presence and movement of the biological indicator in and through the environment and to indirectly monitor the presence and movement of other micro-organisms in the environment. Certain methods of the present invention use this biological indicator to detect and identify fecal contamination sources such as leaking sewer lines, septic tanks, or holding lagoons. For example, the biological indicator of the present invention can be added to a sewer line suspected of leaking. With proper controls in place, detection of the biological indicator in soil, groundwater or streamflow adjacent to the spiked sewer line would indicate the likely presence of a sewer line leak. Such methods can provide data for state and local Total Maximum Daily Load (TMDL) plans.

The biological indicator of the present invention comprises a non-pathogenic micro-organism comprising an exogenous DNA indicator sequence incorporated into the genome of said micro-organism, wherein said exogenous DNA indicator sequence is unique to the species of the biological indicator. The exogenous DNA indicator sequence functions as a detectable signal to indicate the presence of said biological indicator in an environmental system.

The exogenous DNA indicator sequence of the biological indicator may also encode for an indicator protein that functions to produce a detectable signal. In addition to the exogenous DNA indicator sequence, the detectable signal produced by the indicator protein may also be used to indicate the presence of said biological indicator. In one embodiment, the indicator protein produces a visually detectable signal.

The biological indicator of the present invention may comprise a non-pathogenic virus, wherein said non-pathogenic virus comprises an exogenous DNA indicator sequence, wherein said exogenous DNA indicator sequence functions as a detectable signal, wherein said signal is used to indicate the presence of said biological indicator in an environmental system.

The biological indicator of the present invention may comprise a non-pathogenic bacterium, wherein said non-pathogenic bacterium comprises an exogenous DNA indicator sequence, wherein said exogenous DNA indicator sequence encodes for an indicator protein that functions to produce a detectable signal, wherein said signal is used to indicate the presence of said biological indicator in an environmental system.

Numerous aspects of the present invention provide advantages over prior methods of detecting the presence of micro-organisms in the environment. For example, the present invention provides a method for easily detecting the presence of an indicator micro-organism since the biological indicator of the present invention produces a detectable signal. The detectable signal comprises an exogenous DNA indicator sequence. The detectable signal may further comprise a signal produced by an indicator protein produced by the biological indicator. The detectable signal can be used to quantitate the number of biological indicators in a sample.

The biological indicator of the present invention may comprise a variety of micro-organisms. For example, by designing the biological indicator to comprise a particular micro-organism of interest, such as E. coli, methods that use such a biological indicator will more accurately reflect the die-off rate, entry into a dormant like condition such as the VBNC state, and the migration rate of E. coli.

An additional advantage of methods of the present invention is the ability to detect the presence of organisms in a "viable but nonculturable state" (VBNC). The term VBNC refers to indicator bacteria that enter a physiological state characterized as being alive yet unable to undergo growth on nonselective medium sufficient to give rise to visible growth. The viable but nonculturable state has been hypothesized to be a long-term survival mechanism employed by non-sporulating bacteria in response to one or a combination of environmental stresses. Stresses reported to induce the VBNC state include: starvation; temperature shock; heavy metals; visible light; high osmolarity; biocidal agents; high oxygen tension; as well as unknown biological factors. The percentage of cells in a culture that become VBNC vary in response to the specific environmental stress conditions. The VBNC response differs from other bacterial responses such as cell stress, cell starvation, cell wounding, and cell-wall deficient-bacteria in that only VBNC cells do not undergo extensive growth in or on nonselective growth medium (i.e. medium lacking any selective or stress agents and containing nutrients that normally support growth of the strain). VBNC organisms may retain the potential for virulence and may recover after being ingested.

BST methods that rely on culturing bacterial samples are incapable of detecting the presence of organisms that have transformed into a VBNC state. Methods of the present invention are capable of detecting VBNC organisms since the biological indicator of the present invention is capable of producing a detectable signal at all stages of a micro-organism's life. An exogenous DNA indicator sequence that is incorporated into the biological indicator's genome remains present and detectable by PCR methods through out the biological indicator's life (whether the bacterium is growing or not) and into death, until the biological indicator has lysed. An indicator protein, such as Green Flourescent Protein, produced by a biological indicator can continue to produce a detectable signal even if the biological indicator has stopped growing or has died.

An additional advantage of the methods of the present invention results from the incorporation of the exogenous DNA indicator sequence into the genome of the biological indicator of the present invention. Micro-organisms have the potential to genetically interact with other similar micro-organisms and exchange genetic information for example through transfer of episomes. However, genetic information incorporated into the genome of micro-organisms is rarely exchanged between micro-organisms. Since the exogenous DNA indicator sequence of the biological indicator is incorporated into the genome of the biological indicator, the chance of the exogenous DNA indicator sequence being maintained in an environmental system in a different micro-organism is low. Because the biological indicator produces a signal generally not present in related micro-organisms in the environment, the detectable signal should not be obscured by similar background signals. Furthermore, the modification of the recipient micro-organism to create the biological indicator should confer no selective advantage over any strains of similar micro-organisms present in the environmental system.

In one aspect, the biological indicator of the present invention comprises a non-pathogenic micro-organism comprising an exogenous DNA indicator sequence incorporated into the genome of said micro-organism, wherein said exogenous DNA sequence is unique to the species of the biological indicator, wherein said signal can be used to indicate the presence of said biological indicator. In an embodiment, the biological indicator comprises a bacterium. In another embodiment, the biological indicator comprises E. coli. In another embodiment, the biological indicator comprises a virus. The exogenous DNA indicator sequence can encode for an indicator protein that functions to produce a detectable signal, wherein said signal can be used to indicate the presence of said biological indicator in an environmental system. The indicator protein is preferably one that produces a visually detectable signal. In an embodiment, the indicator protein produces a fluorescent signal. In another embodiment, the indicator protein comprises a modified Green Fluorescent Protein. In another embodiment, the indicator protein produces a bioluminescent signal.

In another aspect, the present invention provides a method for detecting and monitoring the transport of micro-organisms in the environment which comprises: adding a biological indicator to an environmental system wherein said biological indicator comprises a non-pathogenic micro-organism comprising an exogenous DNA indicator sequence incorporated into the genome of said biological indicator, wherein said exogenous DNA indicator sequence is unique to the species of the biological indicator, wherein said signal can be used to indicate the presence of said biological indicator; and examining a sample from said environmental system for the detectable signal produced by said biological indicator. In an embodiment, the biological indicator comprises a bacterium. In another embodiment, the biological indicator comprises E. coli. In another embodiment, the biological indicator comprises a virus. The exogenous DNA indicator sequence can encode for an indicator protein that functions to produce a detectable signal. The indicator protein is preferably one that produces a visually detectable signal. In an embodiment, the indicator protein produces a fluorescent signal. In another embodiment, the indicator protein produces a bioluminescent signal. In another embodiment, the indicator protein comprises a modified Green Fluorescent Protein.

In another aspect, the present invention provides a method to determine the state of micro-organisms in environmental systems. This aspect comprises the steps of: adding a biological indicator to an environmental system wherein said biological indicator comprises a non-pathogenic micro-organism comprising an exogenous DNA indicator sequence incorporated into the genome of said micro-organism, wherein said exogenous DNA indicator sequence is unique to the species of the biological indicator, wherein said signal can be used to indicate the presence of said biological indicator; exposing said biological indicator to a desired set of environmental conditions for a period of time; and examining one or more samples from said environmental system for the detectable signal produced by said biological indicator.

In another aspect, the present invention provides a method to determine the effectiveness in an environmental system of biocides and anti-microbial agents. This aspect comprises the steps of: adding a biological indicator to an environmental system wherein said biological indicator comprises a non-pathogenic micro-organism comprising an exogenous DNA indicator sequence incorporated into the genome of said micro-organism, wherein said exogenous DNA indicator sequence is unique to the species of the biological indicator, wherein said signal can be used to indicate the presence of said biological indicator; adding one of the following: a biocide and an anti-microbial agent to an environmental system; and examining a sample from said environmental system for the detectable signal produced by said biological indicator. The step of adding one of the following: a biocide and an anti-microbial agent may occur any time before the step of examining a sample from said environmental system.

In another aspect, the present invention provides a method for identifying a source of fecal contamination comprising the steps of: adding a biological indicator to an environmental system at a first location comprising a potential source of fecal contamination wherein said biological indicator comprises a non-pathogenic micro-organism comprising an exogenous DNA indicator sequence incorporated into the genome of said micro-organism, wherein said exogenous DNA indicator sequence is unique to the species of the biological indicator, wherein said signal can be used to indicate the presence of said biological indicator; waiting a period of time comprising a period sufficient for the biological indicator to travel from said first location to a second location in the environmental system; and examining a sample from said second location for said detectable signal produced by said biological indicator. In an embodiment, the biological indicator comprises a bacterium. In another embodiment, the biological indicator comprises *E. coli*. In another embodiment, the biological indicator comprises a virus. The exogenous DNA indicator sequence can encode for an indicator protein that functions to produce a detectable signal, wherein said signal can be used to indicate the presence of said biological indicator in an environmental system. The indicator protein is preferably one that produces a visually detectable signal. In an embodiment, the indicator protein produces a fluorescent signal. In another embodiment, the indicator protein produces a bioluminescent signal. In another embodiment, the indicator protein comprises a modified Green Fluorescent Protein. In another embodiment, this aspect further comprises the step of concluding that said first location is a source of fecal contamination from the presence of a detectable signal in a sample from said second location. In another embodiment, this aspect further comprises the step of: concluding that said first location is not a source of fecal contamination from the absence of a detectable signal in a sample from said second location.

In another aspect, the present invention provides a method to determine the distribution of bacteria present in materials applied to an environmental system via aerosol. This aspect comprises the steps of: mixing a biological indicator with bacteria containing materials to be applied to the environment via aerosol, wherein said biological indicator comprises a non-pathogenic micro-organism comprising an exogenous DNA sequence incorporated into the genome of said micro-organism, wherein said exogenous DNA indicator sequence is unique to the species of the biological indicator, wherein said signal can be used to indicate the presence of said biological indicator; adding said mixture of biological indicator and bacteria containing materials to an environmental system via aerosol; and examining a sample from said environmental system for the detectable signal produced by said biological indicator. In an embodiment, the biological indicator comprises a bacterium. In another embodiment, the biological indicator comprises *E. coli*. In another embodiment, the biological indicator comprises a virus. The exogenous DNA indicator sequence can encode for an indicator protein that functions to produce a detectable signal, wherein said signal can be used to indicate the presence of said biological indicator in an environmental system. The indicator protein is preferably one that produces a visually detectable signal. In an embodiment, the indicator protein produces a fluorescent signal. In another embodiment, the indicator protein produces a bioluminescent signal. In another embodiment, the indicator protein comprises a modified Green Fluorescent Protein.

In another aspect, the present invention provides a kit for detecting micro-organisms in the environment and for monitoring the transport of micro-organisms in the environment, wherein the kit comprises at least one biological indicator, a detection device capable of detecting the signal produced by the biological indicator. Such a kit may also contain appropriate buffers, growth promoters, growth media, and a recording device.

The biological indicator of the present invention reports its location by producing a detectable signal that can be measured. The biological indicator used in the present method comprises a non-pathogenic micro-organism comprising an exogenous DNA indicator sequence incorporated into the genome of said micro-organism, wherein said exogenous DNA indicator sequence is unique to the species of the biological indicator. The exogenous DNA indicator sequence functions as a detectable signal which can be used to indicate the presence of the biological indicator. The exogenous DNA indicator sequence may also encode for an indicator protein that functions to produce detectable signal. The detectable signal produced by the indicator protein can also be used to indicate the presence of the biological indicator.

In an embodiment of the present invention, the recipient micro-organism comprises *Escherichia coli* strain IA18 (Picard et al. (1999)). This strain was chosen because it is a well-characterized commensal isolate from human feces. Based on rrn RFLP data, this strain belongs to phylogenetic group A (the least virulent of the four phylogenetic groups used to divide the ECOR strains). This strain's virulence was examined by inoculating ten mice and monitoring their health for seven days. None were killed by infection, hence this strain is classified as non-pathogenic. Strain IA18 also does to not produce either hemolysin, mannose-resistant hemagglutinin, or the virulence determinants K1 antigen, sfa/foc operon, pap operon, afa operon, hly operon, aer operon, ibe10 operon. Furthermore, it does not carry any of 25 virulence determinants as assayed for via DNA hybridization. This commensal strain is non-pathogenic, carries no markers that are associated with pathogenic *E. coli* and was randomly chosen, hence it is unlikely that it carries a competitive advantage over other *E. coli* strains. In addition, this strain was tested to confirm that it lacks resistance to six antibiotics: ampicillin, ciprofloxacin, rifampicin, streptomycin, tetracycline, and trimethoprim.

All types of exogenous DNA indicator sequences are contemplated for use in the present invention so long as the sequence is of sufficient length and arrangement that the sequence can be easily identified and distinguished from other DNA sequences contained relevant micro-organisms present in the environment. The exogenous DNA indicator sequence may or may not encode for a protein.

In the case where the exogenous DNA indicator sequence encodes for a protein, the protein may be used to indicate the presence of the biological indicator by producing a detectable signal. While all types of indicator proteins that produce detectable signals are contemplated, an indicator protein that produces a visually-detectable signal, such as bioluminescence or fluorescence, is preferred. Bioluminescence and fluorescence are rarely produced from micro-organisms, so that background signal should not be a significant problem when a fluorescent or bioluminescent signal is produced by the biological indicator.

Green Fluorescent Protein (GFP) and its variants are preferred fluorescent proteins. The Green Fluorescent Protein and its variants have two characteristics that make them preferable for use in the biological indicator of the present invention. They display a strong, stable fluorescence when illuminated by longwave ultraviolet light. The green fluorescence can be detected easily, either visually or with conventional photodetectors. Cells carrying the protein encoded by the gene can be observed and quantitated via epifluorescence microscopy. Because the GFP gene originates from the jellyfish *Aequorea victoria*, any bacteria found to fluoresce green should be evidence of the presence of the engineered *E. coli* (i.e. the biological indicator). Further, because the GFP gene originates from non-bacterial sources, the GFP gene functions as an exogenous DNA indicator sequence, and any bacteria found to contain the GFP gene, as determined using polymerase chain reaction (PCR) amplification with primer sequences originating from the GFP gene should also be evidence of the presence of the engineered *E. coli* (i.e. the biological indicator).

GFP is derived from the jelly fish, *Aequorea victoria*. GFP has been cloned, sequenced and extensively characterized. (Chalfie et al. (1994); see also, U.S. Pat. No. 5,491,084 to Chalfie et al.). A GFP from *Renilla reniformis* has also been characterized. (W. W. Lorenz et al. (1991); R. M. San Pietro et al. (1993)).

In a preferred embodiment, the biological indicator of the present invention comprises *E. coli* strain IA18 and the GFPmut3.1 variant of the *Aequorea victoria* Green Fluorescent Protein. This variant gives very bright green fluorescence when expressed in bacteria because it contains the GFPmut3.1 mutations (Ser-65 to Gly and Ser-72 to Ala) that increase the efficiency of protein folding and chromophore formation at 37° C. (Cormack, B., et al. (1996); Andersen, J. B., et al. (1998)). The GFPmut3.1 fluorophore has an excitation maximum at 501 nm, an emission maximum at 511 nm, and is minimally excited by UV light (Cormack, B., et al. (1996)).

Also contemplated for this invention are DNA sequences which encode red-shifted-GFP (RS-GFP). RS-GFP is an altered form of the GFP which excites at a higher wavelength (excitation: 490 nm, emission: 505 nm). The RS-GFP gene is available on a plasmid, pTU58K, from ClonTech (Palo Alto, Calif.). Another mutant form of GFP displays blue fluorescence. (R. Heim, et al. (1994)). The ECFP gene is available on a plasmid, pECFP, from CloneTech. Another mutant form of GFP displays yellow fluorescence. The EYFP gene is available on a plasmid, pEYFP, from CloneTech. Additional variants of genes that result in products having different excitation and emission wavelengths of light are also contemplated for use in the present invention. Two different biological indicators may have distinguishable exogenous DNA indicator sequences and at the same time the exogenous DNA indicator sequences can encode for indicator proteins that fluoresce at the same or similar wavelengths.

Also contemplated for this invention are biological indicator genes from bioluminescent bacteria. Bioluminescent bacteria contain lux genes, which encode proteins needed to produce a bioluminescent reaction. (E. A. Meighen (1991); E. A. Meighen, (1994)). For example, *Vibrio fischeri* contains a lux operon which contains five genes, luxCDABE, all of which must be efficiently expressed for appropriate functioning of the bioreporter: (R. S. Burlage et al. (1994)). The lux genes are appropriate for use in an aerobic environment.

Using the Biological Indicator to Identify Sources of Fecal Contamination

Figure 2:
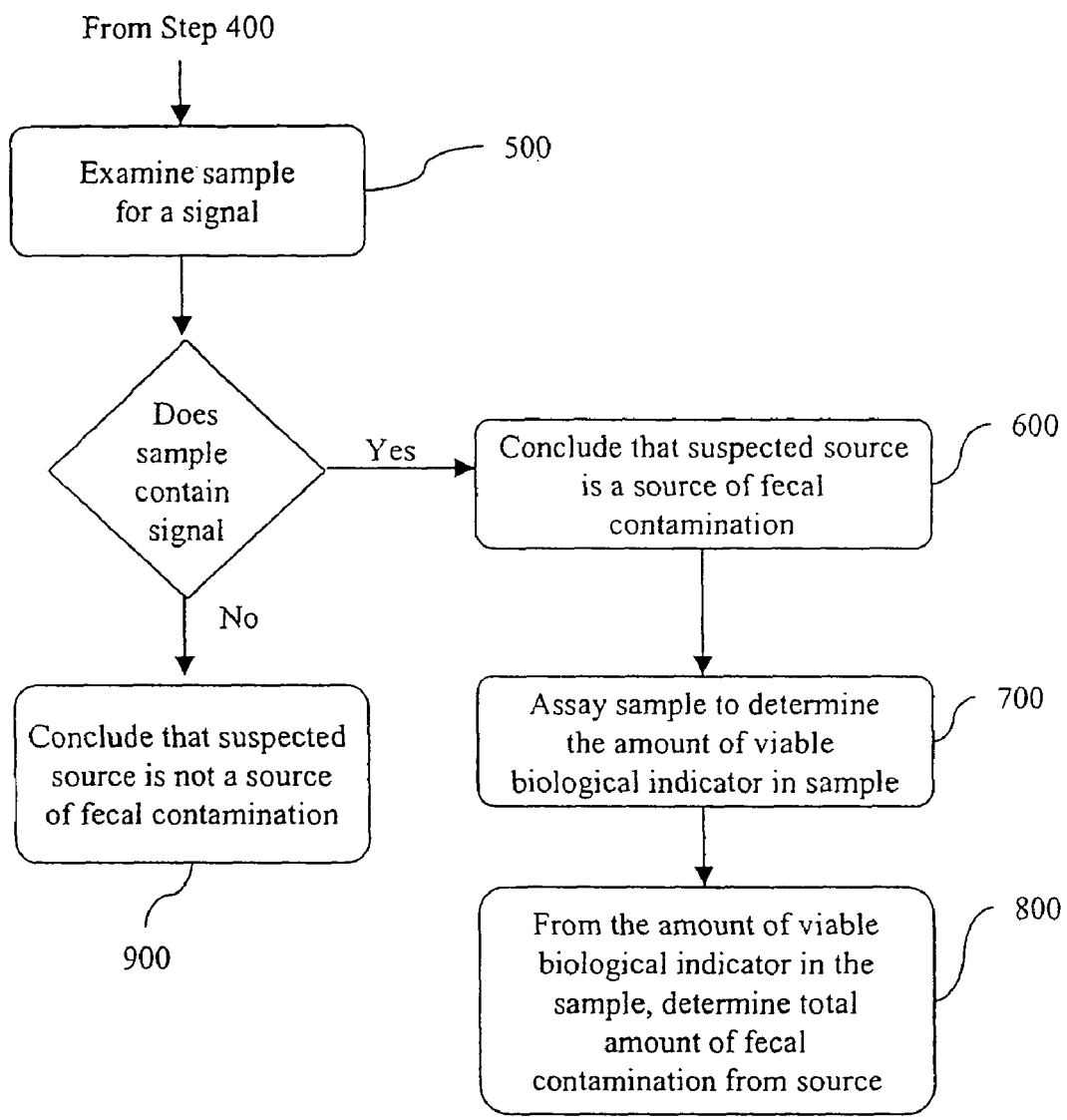

The present invention provides a method for detecting the presence of micro-organisms in the environment which can be used to identify sources of fecal contamination. As shown in FIGS. 1 and 2, the present method begins with an analysis of an environmental system containing a suspected source of fecal contamination (100). Once a potential source of fecal contamination has been identified, the next step is to choose and prepare the biological indicator (200).

A determination of the most appropriate biological indicator to identify potential sources of fecal contamination is based in part on the extent of contamination, size of water shed, availability of watershed information, and type of source of fecal contamination (point and/or nonpoint).

A point source is a pollutant load discharged at a specific location from pipes, outfalls, and conveyance channels from either municipal waste water treatment plants (WWTP) or industrial waste treatment facilities. A nonpoint source is pollution that is not released through pipes but rather originates from multiple sources over a relatively large area. Nonpoint sources can be divided into source activities related to either land or water use including failing septic tanks, improper animal-keeping practices, forest practices, agricultural irrigation runoff, and urban and rural storm water runoff. The transport of pathogens to a water body occurs either directly or indirectly from point and non-point sources.

The limit of detection of the biological indicator of the present invention is equal to the number of biological indicator organisms present in a sample times the recovery efficiency of the biological indicator organisms from the soil. In practice, some biological indicator organisms may be detained in the environmental system or may permanently remain in the environmental system when traveling from the suspected source of fecal contamination. The actual detection limit is dependant on the type of signal. In the case where the signal is the exogenous DNA sequence, materials in a sample such as soil debris may interfere with PCR analysis. Where the signal is a visual produced by an indicator protein, the actual detection limit is dependent upon removal of debris that may obstruct the visual signal and the level of expression of the indicator protein. The theoretical detection limit of the biological indicator can be as low as one micro-organism in a sample.

To estimate typical microbial retention rates and the required sensitivity of detection methods for use of the present method, known amounts of biological indicator organisms can be dosed to laboratory soil columns. Accordingly, the concentration of the biological indicator needed for detection of a signal under typical soil retention rates of an environmental system containing the suspected source of fecal contamination can be determined (200).

As an illustration of estimating typical microbial retention rates using a preferred embodiment of the biological indicator comprising *E. coli* strain IAI8 and GFPmut3.1, a 5.1 to 10.2 cm (2 to 4 inch) soil column is formed in 5.1 cm (2 inch) diameter PVC pipe. Representative soil samples from the area adjacent to the suspected source of fecal contamination are screened through 0.63 cm (¼ inch) mesh, combined to form a composite sample, and adjusted to a moisture content of 15±0.5% (wt. of water/wt. of dry soil). A standard protocol is used to compact the soil columns to a hydraulic conductivity of approximately $10^{-5}$ cm/sec ($3.94 \times 10^{-6}$ inch/sec). A sufficient number of soil columns are prepared so that assays for the biological indicator can be conducted 1, 2 and 4 weeks after the columns are dosed and incubated in the dark at 20° C.

For testing, several pore volumes of elution water are applied to and collected from the columns. The composition of the elution water should simulate the water quality of the natural flow, such as ground water, sewage, lagoon seepage, and the like. Upon dismantling, soil from the columns is sampled, and both the eluted liquid samples and the soil samples are tested for the presence of the biological indicator and fecal coliform bacteria. Analysis of the liquid samples can be conducted according to the membrane filter (MF) test described below. Analysis of the soil samples can be conducted using most probable number (MPN) assays. (Methods of Soil Analysis (1994)). From the general procedures described below, one skilled in the art will be able to analyze for the presence of fecal coliform bacteria and the biological indicator.

In the next step, one must ascertain the dosage of biological indicator required for detection under actual environmental conditions after dilution, dispersion, retardation, and retention in an environmental system (200). Retention of bacteria in soil is influenced by a multitude of biotic, physical and chemical factors (Harvey (1997)) including the composition of the soil, the salt concentration of the leaching fluid (Gannon et al. (1991)), the effects of nutrients on bacterial adsorption characteristics, and flow velocities.

The dosage of biological indicator required for detection under actual environmental conditions can be ascertained from multiple field experiments. One type of field experiment uses dye or conservative tracer studies in an environmental system to gather information related to the flow path, velocity, and dilution effects the could occur to fluid leaking from a sewer line through the soil to a groundwater well. A second type of field experiment uses a preferred embodiment of the biological indicator comprising *E. coli* strain IA18 and GFPmut3.1. In this second type of field experiment, the biological indicator is added to a sanitary sewer at a location known to have cracks that allow leakage, so that the biological indicator can be followed from the cracked region to the surface water. A second site is chosen where the biological indicator is added to a sanitary sewer line in service that is considered to be free of leaks in the section from the addition site to a WWTP. The second location permits estimations of the degree of retardation and retention of biological indicator that can be expected before exit as WWTP influent. When the biological indicator is added to a sanitary sewer known to have cracks that allow leakage, the fate of the dose includes dilution into a target flow, dispersion by tortuous soil pore flow paths, and further dilution by receiving stream flow. When the biological indicator is added to a sanitary sewer flow in a seasoned, leak-free path to a WWTP, the fate of the dose includes dilution in the target flow and perhaps some retention due to attachment to the walls of the pipe.

These trials are used to assess the factors that influence result reliability. Since the biological indicator of the present invention can be quickly detected and measured, repeated trials are used to assess how best to minimize sources of variability during testing. Factors such as large changes in flow or waste characteristics, or entry of a novel waste affects the motility or viability of the biological indicator. Other factors such as the possible presence of pipewall biofilm can hinder collection of data. Existing stream and groundwater flows and velocities can be used to decide where to have downstream sampling locations, and automatic samplers can be used to assess travel times and concentration gradients. In the process of conducting these trials, samples of surface water, groundwater, soil, and WWTP influent are collected and assayed for fecal coliforms and for the biological indicator. Analysis of the samples can be conducted according to the general procedures described below. From the general procedures described below, one skilled in the art would be able to analyze for the presence of fecal coliform bacteria and the biological indicator.

For the next step, the biological indicator is added to a suspected source of fecal contamination (300). Once the biological indicator has been added to a suspected source of fecal contamination, sampling can begin in order to provide a base-line (400). Once a base-line is established, sampling should occur periodically (400). A period of sampling may be once a day for at least a month. A period of sampling may also be once a day for at least a week. A period of sampling may also be once a week for several months. The period for sampling may vary as the time passes from the addition of the biological indicator. For example, sampling may occur every hour for the first 24 hours, and then every 6 hours for the next 48 hours, and then every day for the next week. The period of time sufficient for the biological indicator to travel from the suspected source of fecal contamination to a sampling location can be estimated using dye or conservative tracer studies or from the trials described above.

Analysis of samples for the detectable signal of an exogenous DNA indicator sequence or for a detectable signal of fluorescence can be conducted according to the general procedures described below (500).

If a sample contains a detectable signal, either an exogenous DNA indicator sequence or one produced by an indicator protein, one can conclude that the suspected source of fecal contamination in which the biological indicator was added can be identified as a source of fecal contamination (600).

Once a sample is found to contain a detectable signal; the sample can be assayed to determine the amount of the biological indicator in the sample (700). The total amount of fecal contamination from the identified source can then be estimated (800). Such an estimation would consider factors for retention and dilution as determined in the trials described above. A sample may also be analyzed more than once to determine if the detectable signal can be detected after a period of time.

Sources of fecal contamination can be identified using a method complementary to the preceding method. In the complementary method, the biological indicator can be added to a leak-free sewer line in order to calculate typical retention rates in a leak-free sewer line. After the typical retention rate in a leak-free sewer line is calculated, one can add the biological indicator to a sewer line suspected as a source of fecal contamination. A comparison of the number of biological indicator organisms added to a sewer line suspected as a source of fecal contamination to the number of biological indicator organisms that enter the recipient waste water treatment plant (WWTP) would indicate whether or not the biological indicator organisms were escaping from the sewer line. If one determines that biological indicator organisms are escaping from a sewer line, the sewer line can be identified as a source of fecal contamination.

General Procedures to Analyze Samples Containing the Biological Indicator

The biological indicator and its signal can be detected and assayed using one or more of several methods. The total number of fecal coliforms in water samples containing the biological indicator can be determined using the membrane filter (MF) test. When using the preferred biological indicator comprising *E. coli* strain IA18 and GFPmut3.1, IPTG (a gratuitous $P_{lac}$ inducer) can be added to the medium for the purpose of inducing expression of the gfp gene. Filters containing colonies are then subjected to fluorescent excitation, and the number of fluorescing colonies (i.e. the number of culturable fecal coliforms containing the biological indicator) is scored. A most probable number technique (MPN) can also be used for assays of fecal coliforms retained in the soil.

The total number of biological indicator organisms can be determined via microscopic examination or PCR amplification. As an illustration of microscopic examination, samples containing a preferred biological indicator comprising *E. coli* strain IA18 and GFPmut3.1 are incubated with IPTG for two hours at 37° C. (to induce expression of the gfp gene), diluted, then collected onto black polycarbonate filters. The number of green fluorescing cells that are present can be quantified by examination under an epifluorescent microscope.

For PCR determination, DNA can be isolated from samples using the boiling lysis method. The isolated DNA is subjected to PCR amplification using as primer, sequences originating from the exogenous DNA indicator sequence. Therefore, an amplification signal is generated only if the biological indicator is present. Microscopic detection and PCR amplification can be compared for their relative sensitivity among various types of samples. Microscopic detection of bacteria is expected to be less expensive and more accurate in quantifying cell concentration, but PCR amplification is expected to be more sensitive and not dependent upon fluorescence of the GFP protein.

If the biological indicator of the present invention comprises a cellular organism, the number of viable biological indicator cells can also be determined in one or more of several ways. To describe cells as being VBNC requires using a growth-independent viability assay. One assay used to document the VBNC condition is based upon the ability of a viable cell to undergo elongation in the presence of low levels of yeast extract and a gyrase inhibitor. More recent methods assay for metabolic activities such an active electron transport chain (by use of a redox indicator dye or substrate uptake, or for the presence of molecules that have a high turnover rate, such as mRNA. Additional methods assay for cell membrane potential, plasmolytic response to osmotic stress or cell membrane integrity. For example, the number of viable biological indicator cells can be determined using the Kogure assay (Kogure et al. (1979)). In this assay, viability is indicated by the ability of cells to undergo cell elongation in the presence of low levels of nutrients and an antibiotic that prevents cell division. When examined under the microscope, elongated cells are considered to be viable. As an illustration, a 1 ml volume of a biological indicator comprising *E. coli* strain IA18 and GFPmut3.1 can be dosed with 0.1 ml of 0.1% yeast extract and 0.1% nalidixic acid. After incubation at 25° C. overnight, the biological indicator is collected onto a 0.22 μm black polycarbonate filter and examined for fluorescence. Any green fluorescing and elongated (when compared to untreated samples) cells are counted as being viable biological indicators. Based on these general procedure and others known to one skilled in the art, one can determine the concentration of the biological indicator needed for detection of a signal under typical soil retention rates for other embodiments of the biological indicator disclosed.

Definitions

The term "environment," as used herein, refers to the biotic and abiotic factors that influence the object of interest.

The term "environmental system," as used herein, refers to the region of influence surrounding the location where the biological indicator is added to the environment. An environmental system includes the biotic and abiotic factors in the region that create a certain set of environmental conditions of influence on the biological indicator. Examples of environmental systems that could influence an indicator are the soil, groundwater and air surrounding a lagoon; the soil, stream and sediment adjacent to a sewer line; or the soil, groundwater and adjacent stream near an irrigated agriculture field.

The term "environmental conditions," as used herein, refers to the set of physical, chemical, and biological features particular to the region where a particular object of interest is located. Typical features might include, but are not limited to, temperature, sunlight, pH, toxic compounds, predators, competing populations, and food supply.

The terms "travel" and "transport," as used herein, refer to the movement of micro-organisms, through soils, unconsolidated sediments, rock formations, groundwater, and surface water. Such movement can occur through avection, diffusion, motility, or a combination therein.

The term "biological indicator," as used herein, refers to a micro-organism that indicates its presence by producing a detectable signal. The basis for the capability of the biological indicator to produce a detectable signal is the presence of an exogenous DNA indicator sequence. The exogenous DNA indicator sequence functions as a detectable signal. The exogenous DNA indicator sequence may further encode for an indicator protein that functions to produce a detectable signal.

The term "gene" refers to a DNA sequence that comprises control and coding sequences necessary for the production of a RNA and usually a corresponding polypeptide. With reference to the exogenous DNA indicator sequence, the polypeptide can be encoded by a full length coding sequence or by any portion of the coding sequence so long as, where the indicator protein is desired to perform an activity, the desired activity is retained.

The term "exogenous DNA indicator sequence", as used herein, refers to a DNA sequence which functions as a detectable signal. All types of DNA sequences are contemplated for use in the present invention so long as the sequence is of sufficient length and arrangement that it can be identified and distinguished from all other DNA sequences contained on the genome of relevant micro-organisms present in the environment. This is accomplished by using a DNA sequence that is unique to species of the biological indicator. The exogenous DNA indicator sequence may or may not encode for an indicator protein.

As used herein, an "indicator protein" indicates the presence of the biological indicator. While all types of indicator proteins that produce detectable signals are contemplated, an indicator protein that produces a visually-detectable signal, such as bioluminescence or fluorescence, is preferred. Suitable indicator proteins include, but are not limited to, fluorescent, bioluminescent, or chromogenic agents. A bioluminescent agent produces visible light by a biochemical process. A fluorescent agent produces a longer wavelength of light when it is excited by a shorter wavelength of light. A chromogenic agent produces a visible colored product.

As used herein, the term "vector" is used to refer to nucleic acid molecules that are capable of transferring DNA sequence(s) from one cell to another.

As used herein, the term "polymerase chain reaction" ("PCR") or "PCR analysis" refers to the method of K. B. Mullis disclosed in U.S. Pat. Nos. 4,683,195, 4,683,202 and 4,965,188, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double-stranded target sequence. To effect amplification, the mixture is denatured and the primers then are annealed to their complementary sequences within the target molecule. Following annealing, the primers are extended with a polymerase so as to form a new pair of complementary strands. The steps of denaturation, primer annealing and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified."

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to indicate the presence of the target sequence or to obtain segments of DNA (e.g., genes) for the construction of targeting vectors, cloning of specific genes, searching for expressed genes, etc.

The term "recombinant DNA molecule," as used herein, refers to a DNA molecule which is comprised of segments of DNA joined together by means of molecular biological techniques. A "recombinant organism" or "recombinant strain" refers to a strain of organisms comprising recombinant DNA.

As used herein, the terms "restriction endonucleases" and "restriction enzymes" refer to bacterial enzymes, each of which cleave double-stranded DNA at or near a specific nucleotide sequence.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

As used herein, the term "culture" is used in reference to the in vivo or in vitro growth of organisms, including, but not limited to, bacteria. It is intended that the term encompass any form of microbial culture. It is intended that the term encompass the propagation of microorganisms or other living cells in media and in an environment that is conducive to their growth. Such cultures may be grown in any format, including, but not limited to, agar plates, broths, and semi-solid media, and may be grown in any environment suitable for the organisms cultured (i.e. aerobic, anaerobic, microaerophilic, etc.).

Abbreviations bp=base pairs
GFP=Green Fluorescent Protein
gfp gene=a genetic sequence encoding a Green Fluorescent Protein
IPTG=isopropylthiogalactoside, a gratuitous $P_{lac}$ inducer
kbp=kilobase pairs
Tn=transposon
tnp=transposase-encoding gene A biological indicator according to the present invention can be produced using standard methods to clone DNA, join the fragments, and insert cloned DNA into the genome of the host strain. (Sambrook et al. (1989) *Molecular Cloning, A Laboratory Manual*).

The following illustrates a procedure that can be used to construct a biological indicator of the present invention comprising an *E. coli* strain and an exogenous DNA indicator sequence incorporated into the genome of the *E. coli* that encodes an indicator protein that produces a fluorescent signal. To summarize the procedure, a two-step strategy, can be used to construct a biological indicator comprising an *E. coli* strain and the GFPmut3.1 gene. In the first step, a suicide plasmid is constructed that comprises a mercury-resistant gene and a gfp gene flanked by Tn5 inverted repeats. In the second step, this plasmid is transformed into an *E. coli* strain which does not support growth of the suicide plasmid. The presence of mercury-resistance or green fluorescence protein production indicates the presence of the reporter genes transposed into the genome.

Figure 3:
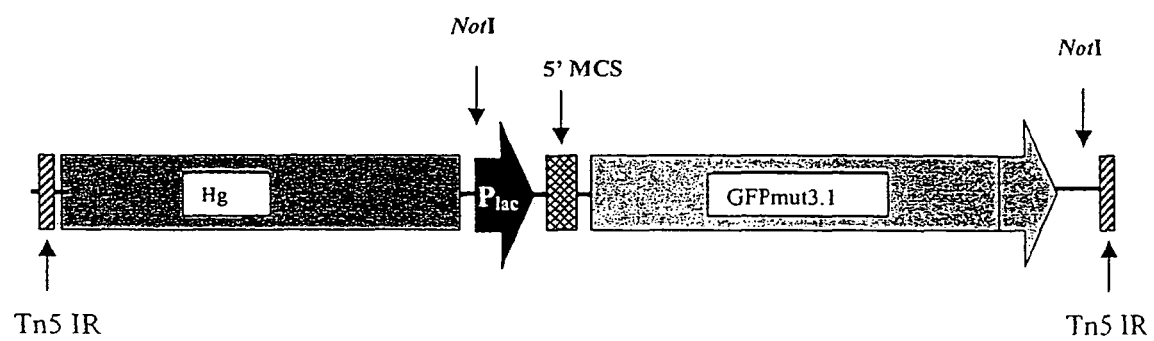
FIG. 3 is a map of an exogenous DNA indicator sequence containing a gene for a green fluorescent protein.

FIG. 3 illustrates a final intergeneric insert that can be located into the genome of the biological indicator wherein Tn5 LR is a DNA sequence comprising a 19 bp inverted repeat that is recognized by Tn5 encoded transposase. The transposase gene will not normally be present in the recipient biological indicator. Hg is the 3 kbp gene from *Serratia marcescens* encoding mercury resistance; $P_{lac}$ is a DNA sequence comprising a promoter from the lactose operon of *E. coli*; 5'MCS is a multiple cloning site located at the 5' end of the gfp structural gene (from Clontech Inc.); gfpmut3.1 represents the DNA sequence comprising an approximately 1.1 kbp green fluorescent gene isolated from jellyfish (*Aequorea victoria*) which has been modified to produce a protein with a long half-life.

Figure 4:
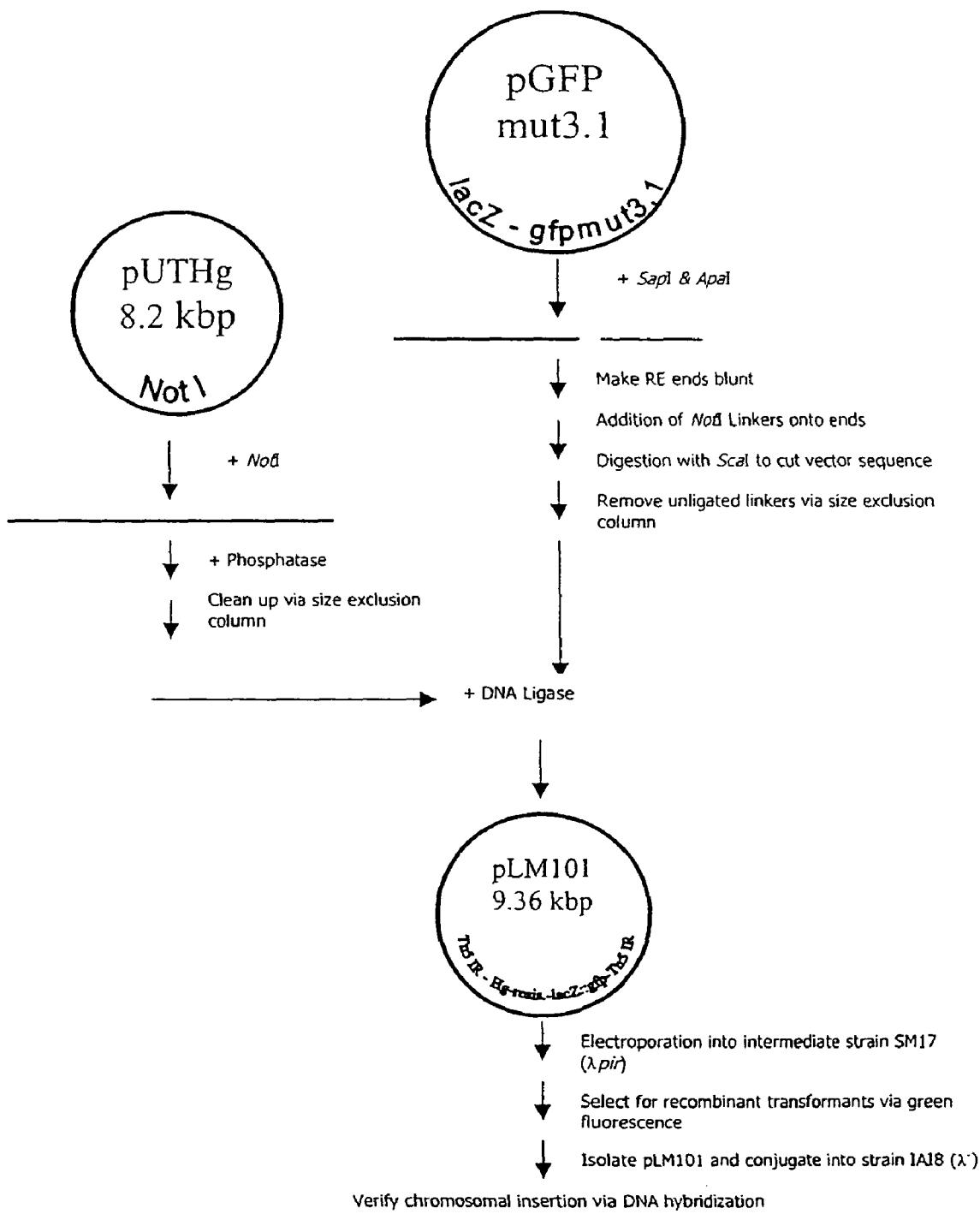
FIG. 4 is a flow diagram showing construction of a GFP plasmid and conjugation of the ep and mercury-resistant genes into the genome of an E. coli.

The following procedure is a detailed description of a procedure that can be used to construct a biological indicator of the present invention comprising an *E. coli* strain and an exogenous DNA indicator sequence incorporated into the genome of the *E. coli* that encodes an indicator protein that produces a fluorescent signal. This procedure is illustrated in FIG. 4.

Initially, the GFPmut3.1 gene under gene expression control of the lacZ promoter is gel-isolated as a 2.25 kbp SapI-ApaI restriction endonuclease (RE) fragment. The ends of this fragment are made blunt-ended. NotI linkers are then ligated onto the ends of this fragment followed by NotI digestion to remove excess linkers. This RE fragment is then cloned into NotI-digested pUTHg. This plasmid comprises the suicide delivery properties of the R6K-based plasmid pGP704 (i.e. the plasmid is only maintained in strains that carry the pir gene from phage lambda). The pUTHg also comprises: 1) the tnp gene that encodes transposase, an enzyme required for transposition of Tn5; 2) an ampicillin-resistant gene; 3) a mercury-resistant gene that is flanked by Tn5 inverted repeats, this is the only gene located between the Tn5 repeats. The NotI cloning site is located between this gene and one of the Tn5 repeats.

Cloning of the gfp gene into the NotI site inserts the gfp gene into the region of the plasmid that can undergo plasmid-controlled transposition.

The constructed plasmid, pUTHg::gfp, is then transferred into *E. coli* strain SM17-1(λpir). Transformants are selected for by growth on ampicillin. Recombinants are selected by growth on phenyl mercuric acetate or screened by observing green fluorescent colonies when viewed under UV illumination.

The engineered suicide plasmid is then isolated from SM17-1(λpir) using an alkaline lysis procedure. This purified plasmid can be transformed into *E. coli* via electroporation or conjugation using standard procedures known to one skilled in the art. Transformants are selected by growth or minimal medium (on which IA18, but not SM17-1, can grow) containing phenyl mercuric acetate.

The recipient strain does not carry the λpir gene; hence the plasmid should not be able to be maintained in the recipient cell. The transformants are grown without selection (i.e. in the absence of ampicillin) for between approximately 1 to 100 generations. The transformants are then separated on Petri plates containing phenyl mercuric acetate. Any colonies that appear will be tested for ampicillin resistance. Colonies that are mercury-resistant and ampicillin-sensitive are considered to be putative chromosomal integrants.

Confirmation of chromosomal integration can be obtained by subjecting DNA purified from putative transformants to RE digestion followed by Southern hybridization, using as probe, a region of the Hg-resistant gene, and a second hybridization, using as probe, a region of the ampicillin-resistant gene. Chromosomal integrants are those that generate a positive signal when probed with the Hg-gene fragment and generate no signal when probed with the ampicillin-resistant gene fragment.

The following example serves to illustrate a preferred embodiment and aspects of the present invention and is not to be construed as limiting the scope thereof. Standard terms are employed, understandable to those skilled in the art.

Example 1

The steps described below were used to construct the *E. coli* strain ES113 for use as a biological indicator of the present invention. To summarize, the gfp gene was cloned into a suicide vector next to a mercury-resistant gene and flanked by Tn5 inverted repeats. This construct was designated as pLM101 and was transformed into a natural coli isolate that does not support replication of the plasmid. After selecting for a recombinant via antibiotic selection, the strain was grown in the absence of antibiotic selection to allow loss of the plasmid.

Figure 5:
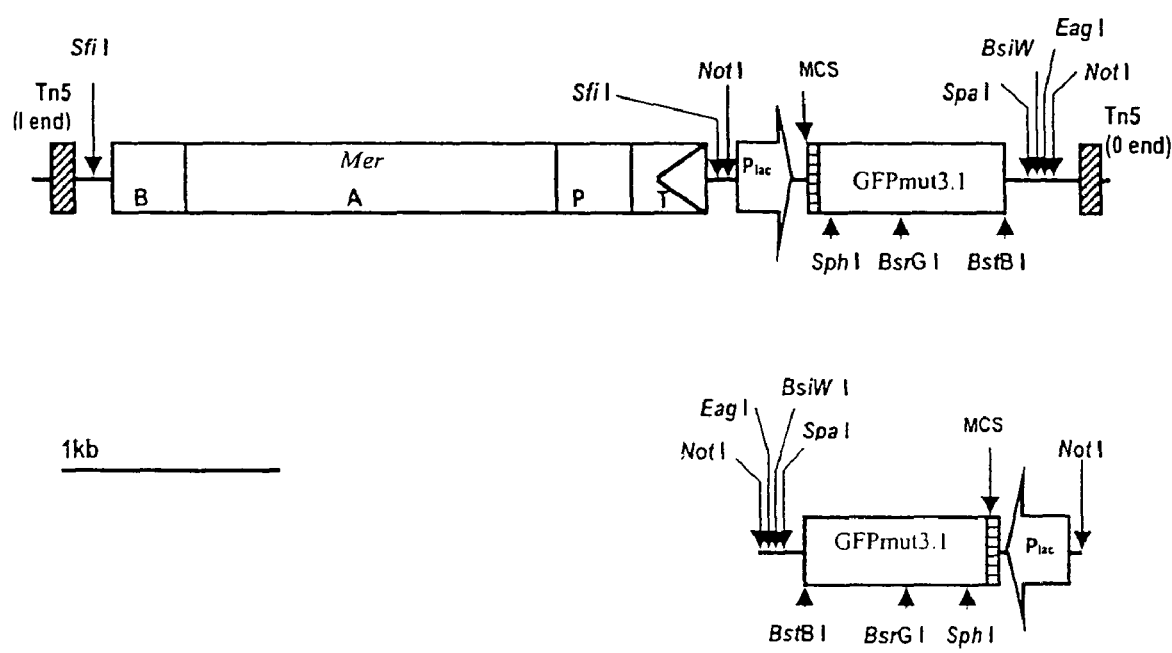
FIG. 5 is a map of two exogenous DNA indicator sequences containing a gene for a green fluorescent protein.

FIG. 5 illustrates the construct designated pLM101, wherein Tn5 I/O comprises a 19 bp inverted repeat that is recognized by the Tn5 encoded transposase; mer comprises an approximately 3 kbp mer TPAB gene and the nzer TPAB gene's native promoter from *Serratia marcescens* encoding mercury-organomercurial compound resistance; $P_{lac}$ is a promoter from the lactose operon of *E. coli*; MCS is a multiple cloning site which lies immediately upstream of a synthetic ribosome binding site; GFPmut3.1 is DNA sequence comprising a 0.74 kbp green fluorescent gene isolated from jellyfish (*Aequorea victoria*) (Clontech Laboratories, Inc.). FIG. 5 shows both possible orientations of the GFPmut3.1 gene relative to mer TPAB.

The following is a detailed description of the steps followed to construct the *E. coli* strain ES113. This procedure is illustrated in FIG. 3.

Initially, the GFPmut3.1 gene under gene expression control of the lacZ promoter was gel-isolated as a 1.06 kbp SapI-ApaI restriction endonuclease (RE) fragment. The ends of this fragment were made blunt using T4 DNA Polymerase. Not I linkers were then ligated onto the ends of this fragment, followed by digestion of the ligation mixture with Not I. The RE fragments with Not I ends were then separated from the free Not I linkers via size column exclusion.

The RE fragment containing gfp flanked by Not I linkers was cloned into NotI-digested pUTHg. The pUTHg gene is derived from pGP704 (Miller and Mekalanos, 1988) which is a suicide plasmid (i.e. the plasmid is only maintained in strains that carry the pir gene from phage lambda) that comprises an R6K ori, a mob gene from RP4, and a MCS from M13tg131. The pUTHg gene also comprises: 1) the tnp* gene that encodes transposase, an enzyme required for transposition of Tn5 (isolated from Tn5-IS50$_R$); 2) an ampicillin-resistant gene (from pBR325); 3) a 3-kb Hind III-EcoRV fragment that carries the intact mer TPAB genes and their native promoter originally isolated from *Serratia marcescens* (Griffin et al., 1987); and 4) Tn5 inverted repeats that flank the mer genes with these being the only genes located between the Tn5 repeats. The NotI cloning site is located between one of the Tn5 repeats and the mer gene promoter.

Cloning of the gfp gene into the NotI site inserted the gfp gene into the region of the plasmid that can undergo plasmid-controlled transposition (i.e. that is flanked by Tn5 ends).

The engineered suicide plasmid carrying the gfp gene was transformed into *E. coli* strain IA18 via conjugation. Transformants were selected by growth on minimal medium containing phenyl mercuric acetate, at a concentration of 2 µg/ml, and screened by observing green fluorescent colonies when viewed under UV illumination.

*E. coli* strain IA18 does not carry the λpir gene; hence the pUTHg plasmid cannot be maintained in this recipient cell. The transformants were grown without selection (i.e. in the absence of ampicillin) for between approximately 1 to 100 generations then separated on Petri plates containing 2 µg/ml phenyl mercuric acetate. Colonies that appear were tested for ampicillin resistance and fluorescence. Colonies that were mercury-resistant, fluoresced green, and were ampicillin-sensitive were putative chromosomal integrants.

Although the present invention has been described with reference to particular embodiments, it should be recognized that these embodiments are merely illustrative of the principles of the present invention. Those of ordinary skill in the art will appreciate that the biological indicator of the present invention may be constructed and implemented in other ways and embodiments. Accordingly, the description herein should not be read as limiting the present invention, as other embodiments also fall within the scope of the present invention.

REFERENCES

American Public Health Association (APHA), American Water Works Association (AWWA), Water Environment Federation (WEF). 1995. *Standard Methods for the Examination of Water and Wastewater*, 19$^{th}$ Edition. Franson, A. H., A. D. Eaton, L. S. Clesceri and A. E. Greenbrg (eds.). American Public Health Association, Washington, D.C.

American Society of Agronomy (ASA) and Soil Science Society of America (SSSA). 1994. Methods of Soil Analysis: Part 2-Microbiological and Biochemical Properties, R. W. Weaver et al. (eds), SSSA Book Series, ASA and SSSA, Madison, Wis.

Andersen, J. B., et al., *Appl. Environ. Microbiol.* 64:2240-2246 (1998).

Bernhard, A. E., and Field, K. G., *Applied. Environmental Microbiol.* 66:1587-1594 (2000).
Burlage R. S., et al., *Ann. Rev. Microbiol.* 48:291-309 (1994).
Chalfie, M., et al., *Science* 263:802-805 (1994).
Cormack, B., et al., *Gene* 173:33-38 (1996).
Gannon, J., et al., *Applied and Environmental Microbiol.* 57:2497-2501 (1991).
Griffin, H. G. et al., *Proc. Natl. Acad. Sci. USA* 84:3112-3116 (1987).
Hagedorn, C. et al., *Applied Environmental Microbiol.* 65:5522-5531 (1999).
Harvey, 1997. In situ and laboratory methods to study subsurface microbial transport, p. 586-599, In C. H. Hurst et al. (eds.), *Manual of Environmental Microbiology*, ASM Press, Washington D.C.
Heim, R., et al., *Proc. Natl. Acad. Sci. USA* 91:12501-12504 (1994).
Kogure, K., Simidu, U., and Taga, N., *Can. J. Microbiol.* 25:415-420 (1979).
Lorenz, W. W., et al., *Proc. Nat'l. Acad. Sci. USA* 88:4438-4442 (1991).
Meighen, E. A., *Microbiol. Rev.* 55:123-142 (1991).
Meighen, E. A., *Ann. Rev. Genet.* 28:117-139 (1994).
Miller, V. L., and Mekalanos, J. J., *J. Bacteriol.* 170:2575-2583 (1988).
Parveen, S., et al., *Applied Enviornmental Microbiol.* 63:2607-2612 (1997).
Parveen, S., et al., *Applied Environmental Microbiol.* 65:3142-3147 (1999).
Picard, B., et al., *Infect. Immun.* 67:5464-553 (1999).
San Pietro, R. M., et al., *Photochem. Photobiol.* 57:635 (1993).
Sinton, L. W., Finlay, R. K., and Hannah, D. J., *New Zealand J. Marine and Freshwater Res.* 32:323-348 (1998).
Wiggins, B. A., *Applied Environmental Microbol.* 62:3997-4002 (1996).
Wiggins, B. A., et al., *Applied Environmental Microbiol.* 65:3483-3486 (1999).
U.S. Environmental Protection Agency. 2001. Protocol for Developing Pathogen TMDLs. EPA 841-R-00-002. Office of Water (4530F), United States Environmental Protection Agency, Washington, D.C. 132 pp.

We claim:

1. A method for identifying a source of fecal contamination comprising:

(a) providing a biological indicator comprising a bacterium or virus and an exogenous DNA indicator sequence, wherein the exogenous DNA indicator sequence is a DNA sequence that is unique to the biological indicator, wherein the exogenous DNA indicator sequence functions as a detectable signal;

(b) adding the biological indicator to an environmental system at a first location comprising a potential source of fecal contamination;

(c) waiting a period of time sufficient for the biological indicator to travel from said first location to a second location in the environmental system; and (d) after the period of time, examining a sample from said second location for said exogenous DNA indicator sequence, wherein detection of the DNA sequence of said exogenous DNA indicator sequence indicates the presence of the biological indicator at the second location of the environmental system.

2. The method of claim 1 further comprising the step of: adding one of the following: a biocide and an anti-microbial agent to an environmental system, wherein the step of adding one of the following: a biocide and an anti-microbial agent occurs before the step of examining a sample.

3. The method of claim 1, wherein said biological indicator comprises *E. coli*.

4. The method of claim 1, further comprising the step of: concluding that said first location is a source of fecal contamination from the presence of the biological indicator in a sample from said second location.

5. The method of claim 1, further comprising the step of: concluding that said first location is not source of fecal contamination from the absence of the biological indicator in a sample from said second location.

6. The method of claim 1, wherein detection of said exogenous DNA indicator sequence comprises detection of the indicator sequence itself using amplification of the indicator sequence.

7. The method of claim 1, wherein the exogenous DNA indicator sequence is selected from the group consisting of a GFP gene, RS-GFP gene, ECFP gene, EYFP gene or the luxCDABE operon of genes.

8. A method for identifying a source of fecal contamination comprising:

(a) providing a biological indicator comprising a bacterium or virus and an exogenous DNA indicator sequence, wherein the exogenous DNA indicator sequence is a DNA sequence that is unique to the biological indicator, wherein the exogenous DNA indicator sequence functions as a detectable signal;

(b) mixing the biological indicator with bacteria containing materials to be applied to an environmental system via aerosol;

(c) adding said mixture of biological indicator and bacteria containing materials to the environmental system via aerosol at a first location comprising a potential source of fecal contamination, wherein the source of fecal contamination is applied to the environmental system via aerosol;

(d) waiting a period of time sufficient for the biological indicator to travel from said first location to a second location in the environmental system; and (e) after the period of time, examining a sample from said second location for said exogenous DNA indicator sequence, wherein detection of the DNA sequence of said exogenous DNA indicator sequence indicates the presence of the biological indicator at the second location of the environmental system.

9. The method of claim 8, wherein said biological indicator comprises *E. coli*.

10. The method of claim 8, wherein detection of said exogenous DNA indicator sequence comprises detection of the indicator sequence itself using amplification of the indicator sequence.

* * * * *